United States Patent [19]

Shutske et al.

[11] Patent Number: 5,179,100
[45] Date of Patent: Jan. 12, 1993

[54] 4,5-DIHYDROPYRAZOLO[3,4-A]ACRIDINES

[75] Inventors: Gregory M. Shutske, Flemington, N.J.; John D. Tomer, IV, Perkasie, Pa.

[73] Assignee: Hoechst-Roussel Pharmaceuticals inc., Somerville, N.J.

[21] Appl. No.: 848,558

[22] Filed: Mar. 9, 1992

[51] Int. Cl.$^5$ .................. A61K 31/44; C07D 471/04; C07D 47/06
[52] U.S. Cl. .................................... 514/287; 546/64
[58] Field of Search ........................ 546/64; 514/287

[56] References Cited

PUBLICATIONS

Boyer et al., J. Chem. Research, Synthesis of Pyrazolo[a]acridin-9(10H)–ones, 1990, pp. 350–351.

*Primary Examiner*—C. Warren Ivy
*Assistant Examiner*—P. G. Spivack
*Attorney, Agent, or Firm*—Tatsuya Ikeda

[57] ABSTRACT

There are disclosed various compounds of the formula below,

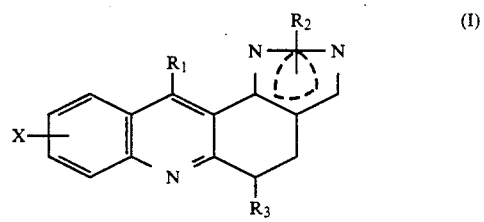

where the parameters $R_1$, $R_2$ and $R_3$ are as defined in the specification, which compounds are useful as analgesic agents.

21 Claims, No Drawings

4,5-DIHYDROPYRAZOLO[3,4-A]ACRIDINES

The present invention relates to compounds having Formula I depicted below,

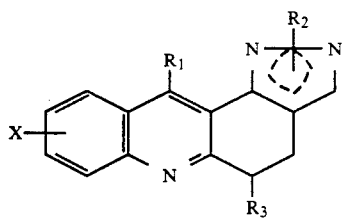

where,

X is hydrogen, loweralkyl, loweralkoxy, halogen or trifluoromethyl;

$R_1$ is hydrogen or $-NR_4R_5$, each of $R_4$ and $R_5$ being independently hydrogen, loweralkyl or arylloweralkyl;

$R_2$, which is a substituent on one of the two nitrogen atoms of the pyrazole ring, is hydrogen, loweralkyl, loweralkoxy, aryl, arylloweralkyl, cyanoloweralkyl, $-C_mH_{2m}COOR_6$, $-NR_7R_8$, $-C_nH_{2n}NR_7R_8$ or $-N=CH$-aryl, $R_6$ being hydrogen or loweralkyl, m, being an integer of 1 to 3, each of $R_7$ and $R_8$ being independently hydrogen or loweralkyl, and n being an integer of 2 to 4; and $R_3$ is hydrogen or $-CHOH$-aryl; which compounds are useful as analgesic agents.

Compounds I subsume compounds of Formula II and those of Formula III depicted below where the parameters X and $R_2$ through $R_5$ are as defined above.

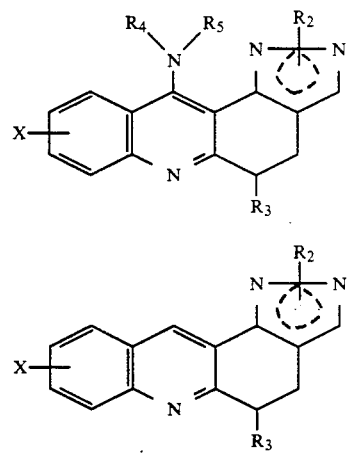

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, iso-butyl, sec-butyl and straight- and branched-chain pentyl and hexyl.

The term aryl in each occurrence shall mean a phenyl group optionally mono-substituted with loweralkyl, loweralkoxy, halogen, or trifluoromethyl.

The term halogen shall means fluorine, chlorine, bromine or iodine.

Throughout the specification and the appended claims, a given chemical formula or name shall encompass all geometric, stereo, optical and tautomeric isomers where such isomers exist.

The compounds of this invention can be prepared by utilizing one or more of the synthetic steps described below.

Throughout the description of the synthetic steps, the notations X and $R_1$ through $R_8$ shall have the respective meanings given about unless otherwise stated or indicated.

STEP A

A compound of Formula III (where $R_1$ is not $-NH_2$) is allowed to react with N,N-dimethylformamide dimethyl acetal to afford a compound of Formula IV. It is convenient to conduct this reaction in an excess of said acetal under a reflux condition.

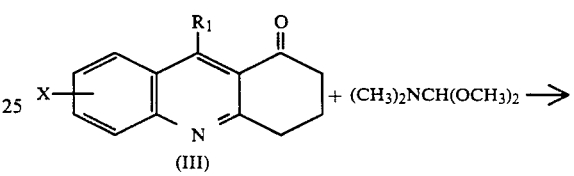

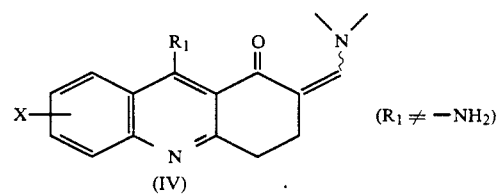

Where $R_1$ is $-NH_2$, the product of this reaction is a compound depicted by Formula IV a below:

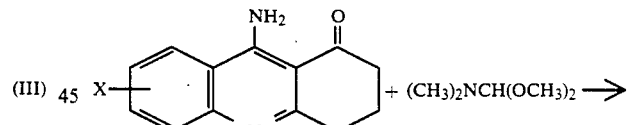

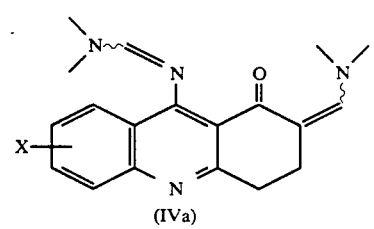

As to the preparation of compound III where $R_1$ is not hydrogen, the reader is referred, for instance, to Shutske et al., U.S. Pat. No. 4,631,286.

The compound of Formula III where $R_1$ is hydrogen can be prepared by conducting the reaction depicted below. Typically it is convenient to conduct this reaction in the present of a suitable acid such as benzesulfonic acid and a suitable solvent such as toluene at a temperature of about 100° to 150°.

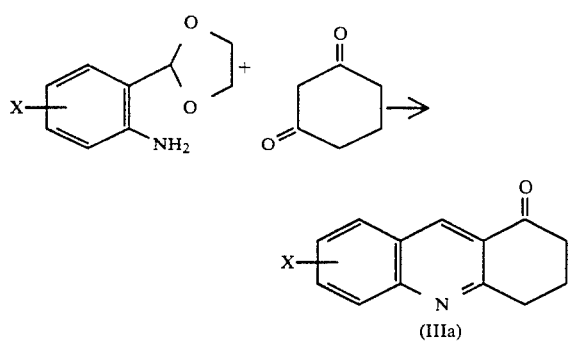

(IIIa)

STEP B

Compound IV or compound IVa is allowed to react with hydrazine to afford a compound of Formula V.

(IV) or (IVa) + $H_2NNH_2$ ⟶

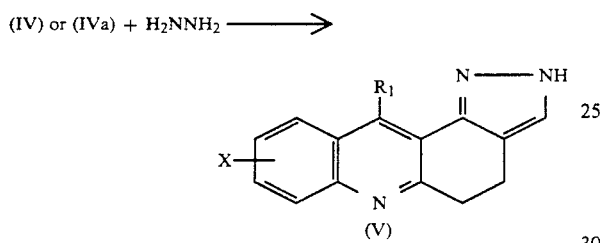

(V)

This reaction is typically conducted in a suitable solvent such as ethanol at a temperature of about 50° to 100°.

STEP C

Compound V is allowed to react with a chloro or bromo compound of the formula, $R_9$-Hal where Hal is chlorine or bromine and $R_9$ is loweralkyl, loweralkenyl, arylloweralkyl, cyanoloweralkyl,

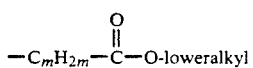

or $-C_nH_{2n}NR_7R_8$ to afford a compound of Formula VI.

(V) + $R_9$—Hal ⟶ 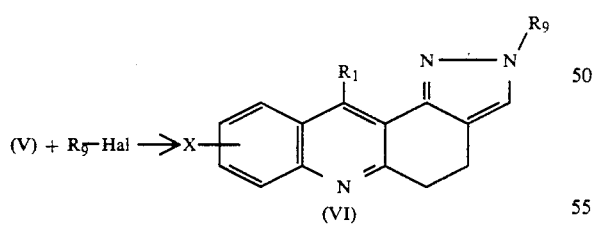

(VI)

This reaction is typically conducted with the aid of a strong base such as sodium hydride to obtain the corresponding anion of compound V which then reacts with the halogen compound to afford compound VI. This reaction is typically conducted in a suitable medium such as dimethylformamide at the temperature of about 0° to 50°.

STEP D

A compound of Formula VIa which is obtained from Step C above is hydrolyzed in a routine manner known to the art to afford a compound of Formula VII. Typically this reaction is conducted with the aid of potassium hydroxide.

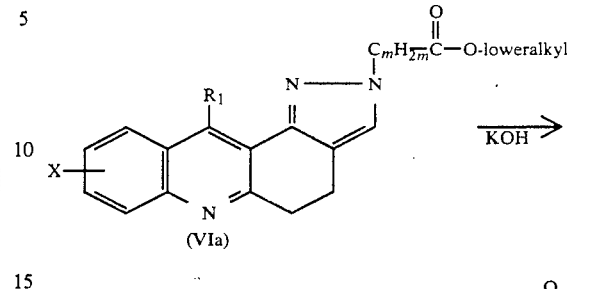

(VIa)

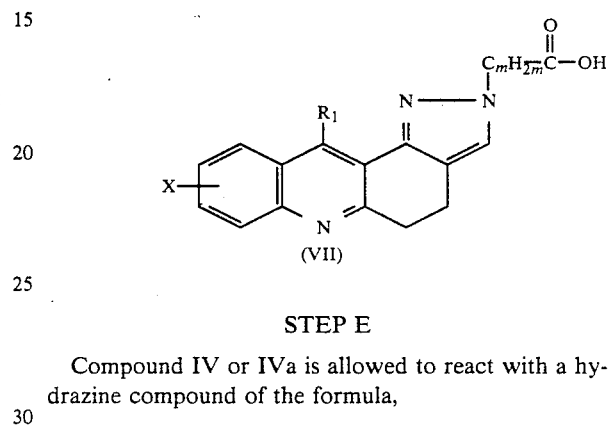

(VII)

STEP E

Compound IV or IVa is allowed to react with a hydrazine compound of the formula,

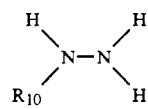

where $R_{10}$ is loweralkyl, loweralkenyl, aryl, arylloweralkyl or cyanoloweralkyl to afford compounds of Formula VIII and IX. The two products can be separated from each other by methods known to the art. This reaction is conducted typically in the presence of a suitable solvent such as ethanol at a temperature of about 50° to 100°.

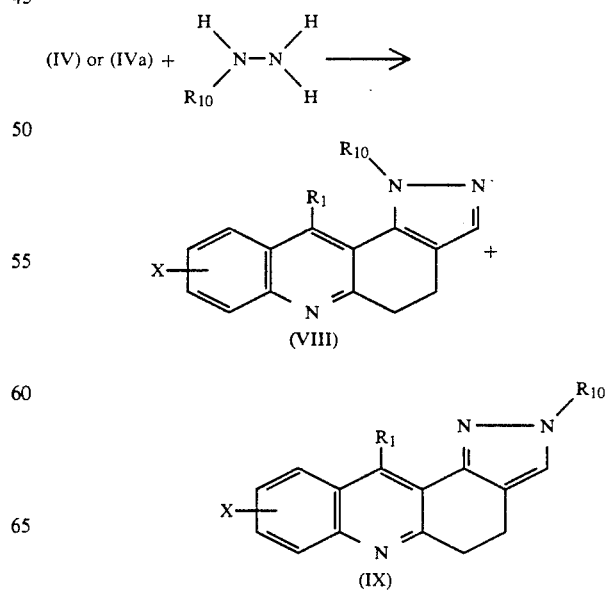

(VIII)

(IX)

STEP F

Compound V is allowed to react with hydroxylamine-O-sulfonic acid to afford a compound of Formula X. This reaction is typically conducted with the aid of aqueous sodium hydroxide in a suitable medium such as ethanol at a temperature of 50° to 100°. When the group R₁ is hydrogen, this reaction affords both a compound of Formula Xa and a compound of Formula Xb.

(V) + H₂NOSO₃H ⟶

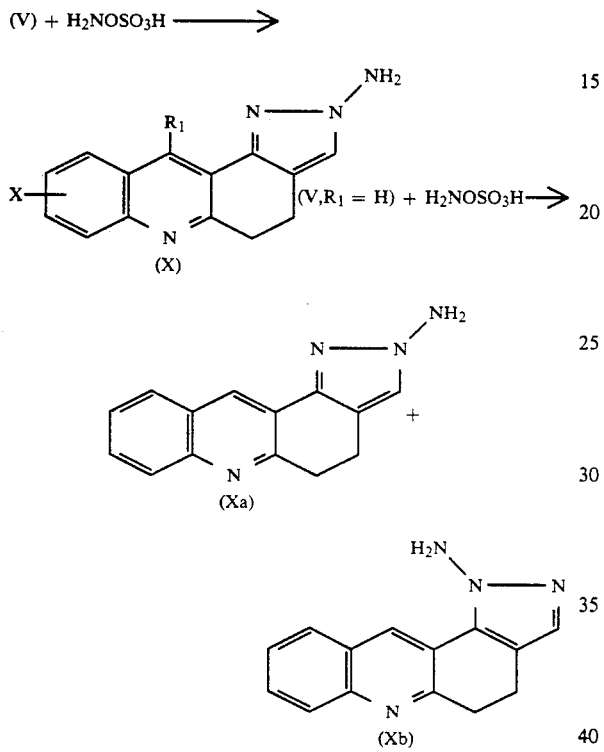

When the above reaction is not complete and hence the resultant product contains a substantial amount of the starting compound V, one can allow the product to further react with benzaldehyde whereby compound X is converted to the corresponding benzylidene compound, (see Step G below for details), and the latter is then converted back to compound X, for instance, by refluxing it in hydrazine monohydrate in a suitable solvent such as n-butanol. This method can serve to separate compound Xa from compound Xb, because compound Xb does not react with benzaldehyde.

STEP G

Compound X is allowed to react with a benzaldehyde compound of Formula XI where Y is hydrogen, loweralkyl, loweralkoxy, halogen or trifluoromethyl to afford compounds of Formula XII and XIII.

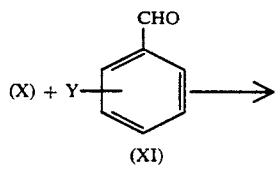

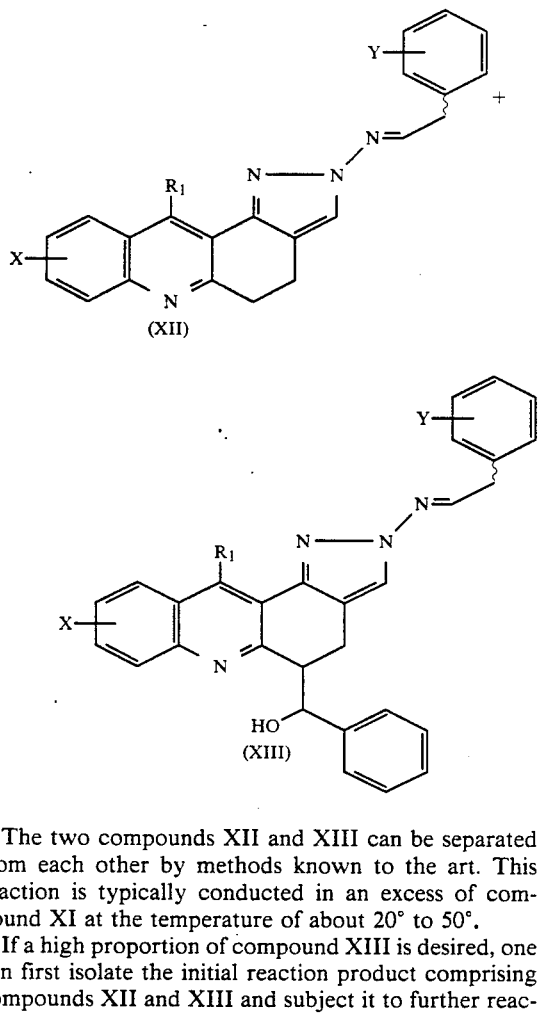

The two compounds XII and XIII can be separated from each other by methods known to the art. This reaction is typically conducted in an excess of compound XI at the temperature of about 20° to 50°.

If a high proportion of compound XIII is desired, one can first isolate the initial reaction product comprising compounds XII and XIII and subject it to further reaction with compound XI to increase the yield of compound XIII.

The compounds of Formula I of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 1 shows results of the test for some of the compounds of this invention along with a result for a reference compound. The tests were conducted at the subcutaneous dose of 20 mg/kg.

TABLE 1

| Compound | PQW Activity % Inhibition |
|---|---|
| 11-amino-4,5-dihydro-2-methyl-2H-pyrazolo[3,4-a]acridine | 54% |
| 11-amino-4,5-dihydro-2-ethyl-2H-pyrazolo[3,4-a]acridine | 67% |
| 11-amino-4,5-dihydro-1-phenyl-1H-pyrazolo[3,4-a]acridine | 48% |
| 11-amino-4,5-dihydro-2H-pyrazolo[3,4-a]acridine-2-acetic acid hydrochloride hemihydrate | 58% |
| 11-amino-4,5-dihydro-2-(2-dimethylaminoethyl)-2H-pyrazolo[3,4-a]acridine | 59% |
| 11-amino-4,5-dihydro-2H-pyrazolo[3,4-a]acridine-2-acetonitrile (Reference Compound) | 47% |

TABLE 1-continued

| Compound | PQW Activity % Inhibition |
|---|---|
| Aspirin at 33 mg/kg, s.c. | 50% |

Effective quantities of the compounds of the invention may be administered to a patient by any of the various methods, for example, orally as in capsule or tablets, parenterally in the from of sterile solutions or suspensions, and in some cases intravenously in the for of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acid such as hydrochloric, hydrobromic, sulfuric, nitric, phosphoric and perchloric acids, as well as organic acids such tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
11-Amino-4,5-dihydro-1H-pyrazolo[3,4-a]acridine;
11-Amino-4,5-dihydro-2-ethyl-2H-pyrazolo[3,4-a]acridine;
11-Amino-4,5-dihydro-2-propyl-2H-pyrazolo[3,4-a]acridine;
11-Amino-4,5-dihydro-2-(2-phenylethyl)-2H-pyrazolo[3,4-a]acridine;
11-Amino-4,5-dihydro-2H-pyrazolo[3,4-a]acridine-2-acetic acid ethyl ester;
11-Amino-4,5-dihydro-2H-pyrazolo[3,4-a]acridine-2-acetic acid;
11-Amino-4,5-dihydro-2(2-dimethylaminoethyl)-2H-pyrazolo[3,4-a]acridine;
11-Amino-2-benzyl-4,5-dihydro-2H-pyrazolo[3,4-a]acridine;
11-Amino-4,5-dihydro-2H-pyrazolo[3,4a]acridine-2-acetronitrile;
11-Amino-4,5-dihydro-2-(2-propenyl)-2H-pyrazolo[3,4-a]acridine;
11-Amino-4,5-dihydro-1-methyl-1H-pyrazolo[3,4-a]acridine;
11-Amino-4,5-dihydro-2-methyl-2H-pyrazolo[3,4-a]acridine;
11-Amino-4,5-dihydro-1-phenyl-1H-pyrazolo[3,4-a]acridine;
2,11-Diamino-4,5-dihydro-2H-pyrazolo[3,4-a]acridine;
11-Amino-2-benzylideneamino-4,5-dihydro-α-phenyl-2H-pyrazolo[3,4-a]acridine-5-methanol;
4,5-Dihydro-2H-pyrazolo[3,4-a]acridine;
2-Amino-4,5-dihydro-2H-pyrazolo[3,4-a]acridine; and
1-Amino-4,5-dihydro-1H-pyrazolo[3,4-a]acridine;

The following examples are presented in order to illustrate the present invention.

EXAMPLE 1

II-Amino-4,5-dihydro-1H-pyrazolo[3,4-acridine hydrochloride hydrate 3,4-Dihydro-2-[(dimethylamino)methylene]-9-[[(dimethylamino)methylene]amino]acridin-1-(2H)-one (3.0 g) was refluxed for 30 min in 50 mL of EtOH containing 2.0 g of hydrazine. At the end of this time the solvent was evaporated under reduced pressure and then the reside was adhered to silica with MeOH. Purification by flash chromatography (5% MeOH/EtOAc) gave a material which was converted to the hydrochloride in aqueous 5% hydrochloric acid. Recrystallization from MeOH/Et$_2$O gave 1.72 g mp 360° (d). This material was combined with the product of another run and recrystallized again from MeOH/Et$_2$O.

Analysis: Calculated For $C_{14}H_{12}N_4 \cdot HCl \cdot 0.25H_2O$: 60.65%C, 4.74%H, 20.21%N, Found: 60.77%C, 4.74%H, 20.24%N.

EXAMPLE 2

11-Amino-4,5-dihydro-2-ethyl-2H-pyrazolo[3,4-a]acridine

To a solution of 11-amino-4,5-dihydro-1H-pyrazolo[3,4-a]acridine (3.0 g) in dry DMF (90 ml) was added NaH (60%)(0.63 g) slowly. The reaction was stirred at room temperature for a half hour, bromoethane (1.2 ml) was added and the reaction was stirred at room temperature overnight.

The reaction was diluted with water (210 ml), stirred at room temperature for one hour, filtered, washed well with water, and air dried to yield 3.33 g of product. This was combined with a 1.0 g probe run and recrystallized from ethyl acetate and dried under high vacuum and refluxing xylenes overnight to yield 3.0 g of beige crystals, m.p. 240°–242° C.

Analysis:
Calculated for $C_{16}H_{16}N_4$: 72.70%C, 6.10%H, 21.20%N, Found: 72.28%C, 5.98%H, 20.97%N.

EXAMPLE 3

11-Amino-4,5-dihydro-2-propyl-2H-pyrazolo[3,4-a]acridine

To a solution of 11-amino-4,5-dihydro-1H-pyrazolo[3,4-a]acridine (3.0 g) in dry DMF (90 ml) was added NaH (60%)(0.63 g) slowly. The reaction was stirred at room temperature for a half hour, iodopropane (1.58 ml) was added and the reaction was stirred at room temperature overnight.

The reaction was diluted with water (210 ml), stirred at room temperature for one hour, filtered, washed well with water, and air dried to yield 3.53 g of product. This was combined with a 1.0 g probe run and recrytallized from ethyl acetate and dried under high vacuum and refluxing xylenes overnight to yield 3.03 g of off-white fluffy crystals, m.p. 225°–226° C.

Analysis: Calculated for $C_{17}H_{18}N_4$: 73.35%C, 6.52%H, 20.13%N, Found: 73.09%C, 6.52%H, 19.96%N.

EXAMPLE 4

11-Amino-4,5-dihydro-2-(2-phenylethyl)-2H-pyrazolo[3,4-a]acridine

To a solution of 11-amino-4,5-dihydro-1H-pyrazolo[3,4-a]acridine (4.36 g) in dry DMF (130 ml) was slowly added 922 mg of NaH (60%). The reaction was stirred at room temperature for one hour, then (2-bromoethyl)benzene (3.23 ml) was added and the reaction stirred for four hours. An additional 230 mg of NaH (60%) was added, and then the reaction was stirred for a half hour, after which 0.8 ml of (2-bromoethyl)benzene was added and the reaction was stirred at room temperature overnight.

The reaction was diluted with water (305 ml), stirred at room temperature for one hour, filtered, washed well with water, and air dried to yield 6.08 g of product. Recrystallization from ethyl acetate and drying under high vacuum and refluxing xylenes overnight yielded 2.03 g of beige fluffy crystals, m.p. 238°–239° C.

Analysis: Calculated for $C_{22}H_{20}N_4$: 77.62%C, 5.92%H, 16.46%N, Found: 77.51%C, 5.95%H, 16.51%N.

EXAMPLE 5

11-Amino-4,5-dihydro-2H-pyrazolo[3,4-a]acridine-2-acetic acid ethyl ester

To a solution of 11-amino-4,5-dihydro-1H-pyrazolo[3,4-a]acridine (10 g) in dry DMF (300 ml) was added NaH (60%)(2.12 g) slowly. The reaction was stirred at room temperature for two hours, ethyl bromoacetate (6.0 ml) was added and the reaction was stirred for one hour.

The reaction was diluted with water (700 ml), stirred at room temperature for one hour, filtered, washed well with water, and air dried to yield 12.48 g of product. A 4.0 g portion was recrystallized from ethanol and dried under high vacuum and refluxing xylenes overnight to yield 2.47 g of an off-white fluffy solid, m.p. 249° C. (dec.).

Analysis:
Calculated for $C_{18}H_{18}N_4O_2$: 67.07%C, 5.63%H, 17.38%N, Found: 67.21%C, 5,54%H, 17.35%N.

EXAMPLE 6

11-Amino-4,5-dihydro-2H-pyrazolo[3,4-a]acridine-2-acetic acid hydrochloride hemihydrate To a solution of potassium hydroxide (6.73 g) in methanol (200 ml) was added 11-amino-4,5-dihydro-2H-pyrazolo[3,4-a]acridine-2-acetic acid ethyl ester. The reaction was stirred at room temperatures for 1.5 hours, heated until homogeneous, cooled, and concentrated. The resulting solid was stirred in 5% HCl for a half hour, filtered, washed with water, and air dried to yield 8.07 g of product. Recrystallization from methanol and drying under high vacuum and refluxing xylenes for 36 hours yielded 5.0 g of an almond colored solid, m.p. 194° C. (dec.).

Analysis:
Calculated for $C_{16}H_{14}N_4O_2 \cdot HCl \cdot 0.5H_2O$: 56.55%C, 4.75%H, 16.50%N, Found: 56.66%C, 4.85%H, 16.43%N.

EXAMPLE 7

11-Amino-4,5-dihydro-2-(2-dimethylaminoethyl)-2H-pyrazolo [3,4-a]acridine

To a solution of 11-amino-4,5-dihydro-1H-pyrazolo[3,4-a]acridine (8.0 g) in dry DMF (240 ml) was slowly added NaH (60%)(1.69 g). The reaction was stirred at room temperature for one hour, 2-dimethylaminoethylchloride (4.64 g) was added and stirring was continued for two hours. An additional 4.64 g of 2-dimethylaminoethylchloride was added and the reaction was stirred at room temperature overnight.

The reaction was diluted with saturated $K_2CO_3$ (500 ml), extracted with ethyl acetate, dried ($MgSO_4$), and concentrated. The resulting solid was adhered to silica (50 g), flash chromatographed (10%$Et_3$N/EtOAc), and triturated (diethyl ether) to yield 5.74 g of a white crystalline solid. Recrystallization from ethyl acetate and drying under high vacuum and refluxing toluene overnight yielded 4.48 g of white crystals, m.p. 177°–178° C.

Analysis: Calculated for $C_{18}H_{21}N_5$: 70.33%C, 6.89%H, 22.78%N, Found: 70.31%C, 6.86%H, 22.92%N.

EXAMPLE 8

11-Amino-2-benzyl-4,5-dihydro-2H-pyrazolo[3,4-a]acridine

To a solution of 11-amino-4,5-dihydro-1H-pyrazolo[3,4-a]acridine (2.36 g) in dry DMF (90 ml) was added NaH (60%)(0.50 g) slowly. The reaction was stirred at room temperature for 15 minutes and then benzyl bromide (1.88 g) was added and the reaction was stirred an additional 15 minutes. At the end of this time the product was precipitated with water, filtered off, washed well with water, and air dried to yield a product which was further purified by flash chromatography (5% Et$_3$N-EtOAc). The product-containing fractions were combined, concentrated, and recrystallized from EtOAc to give 2.35 g, mp 206°-207°.

Analysis:

Calculated for C$_{21}$H$_{18}$N$_4$: 77.27%C, 5.56%H, 17.17%N, Found: 77.01%C, 5.58%H, 17.22%N.

EXAMPLE 9

11-Amino-4,5-dihydro-2H-pyrazolo[3,4-a]acridine-2-acetonitrile

To a solution of 11-amino-4,5-dihydro-1H-pyrazolo[3,4-a]acridine (8.0 g) in dry DMF (240 ml) was slowly added NaH (60%)(1.68 g). The reaction was stirred at room temperature for one hour, chloroacetonitrile (2.72 ml) was added and stirring was continued for 1.5 hours. An additional 1.36 ml of chloroacetonitrile was added and the reaction was stirred at room temperature overnight.

The reaction was diluted was water (275 ml), stirred for a half hour, filtered, washed with water, and air dried to yield 6.67 g of product. The solid was adhered to silica, flash chromatrographed (18:2:1 toluene/methanol/triethylamine), recrystallized from methanol, and dried under high vacuum and refluxing xylenes overnight to yield 1.56 g of a fluffy off-white solid, m.p. 251° C.(dec.).

Analysis: Calculated for C$_{16}$H$_{13}$N$_5$: 69.80%C, 4.76%H, 25.44%N, Found: 69.76%C, 4.74%H, 25.31%N.

EXAMPLE 10

11-Amino-4,5-dihydro-2-(2-propenyl)-2H-pyrazolo[3,4-a]acridine

To a solution of 11-amino-4,5-dihydro-1H-pyrazolo]3,4-a]acridine (4.46 g) in dry DMF (133 ml) was slowly added NaH (60%)(937 mg). The reaction was stirred at room temperature for one hour, allyl bromide (2.10 ml) was added and stirring was continued for a half hour. The reaction was diluted with water (500 ml), stirred at room temperature for one hour, filtered, washed well with water, air dried and triturated with diethyl ether to yield 4.11 g of product. This was combined with a probe run and recrystallization from ethyl acetate and drying under high vacuum and refluxing xylenes overnight yielded 2.76 g of beige fluffy crystals, m.p. 226°226.5° C.

Analysis: Calculated for C$_{17}$H$_{16}$N$_4$: 73.89%C, 5.84%H, 20.27%N, Found: 73.66%C, 5.77%H, 20.19%N.

EXAMPLE 11

11-Amino-4,5-dihydro-1-methyl-1H-pyrazolo[3,4-a]acridine 3,4-Dihydro-2-[(dimethylamino)methylene]-9-[[(dimethylamino)methylene]amino]acridin-1-(2H)-one (3.0 g) was refluxed for 60 min in 150 mL of EtOH containing 8.0 g of methylhydrazine. At the end of this time the solvent was evaporated under reduced pressure and then the residue was adhered to silica with MeOH. Purification by flash chromatography (toluene:MeOH:Et$_3$N, 19:1:1) gave 1.71 g of material which was pure to TLC. This was combined with the product of another run of smaller size and recrystallized from toluene to give analytically pure product, mp 240° (d).

Analysis: Calculated for C$_{15}$H$_{14}$N$_4$: 71.98%C, 5.63%H, 22.39%N, Found: 71.95%C, 5.63%H, 22.09%N.

EXAMPLE 12

11-Amino-4,5-dihydro-2-methyl-2H-pyrazolo[3,4-a]acridine 3,4-Dihydro-2-[((dimethylamino)methylene]-9-[[(dimethylamino)methylene]amino]acridin-1-(2H)-one (12.0 g) was refluxed for 60 min in 150 mL of EtOH containing 8.0 g of methylhydrazine. At the end of this time the solvent was evaporated under reduced pressure and then the residue was adhered to silica with MeOH. Purification by flash chromatography (toluene:MeOH:Et$_3$N, 19:1:1) gave 4.93 g of material which was pure to TLC. Recrystallization from MeOH gave analytically pure product, mp 280° (d).

Analysis: Calculated for C$_{15}$H$_{14}$N$_4$: 71.98%C. 5.63%H, 22.39%N, Found: 71.89%C, 5.75%H, 22.39%N.

EXAMPLE 13

11-Amino-4,5-dihydro-1-phenyl-1H-pyrazolo[3,4-a]acridine

To a hot solution of phenylhydrazine hydrochloride (35.85 g) in absolute ethanol (1.5 L) was added powdered KOH (15.5 g). The reaction was refluxed for 2 hours, cooled and filtered. The filtrate was placed in a 3L round bottom flask and 3,4-dihydro-2-[(dimethylamino)methylene]-9-[[(dimethylamino)methylene]amino]acridin-1-(2H)-one (20 g) was added. The reaction mixture was refluxed for 1.5 hours, concentrated, adhered to silica (107 g), flash chromatographed (1.5 % Et$_3$N/EtOAc) and triturated (pentane/ethanol) to yield 7.82 g of 11-formamido-4,5-dihydro-1-phenyl-1H-pyrazolo[3,4-a]acridine. This was stirred in a solution of KOH (6.5 g) in methanol (189 ml) overnight. The solid was filtered, washed with methanol and air dried to yield 6.94 or product. Recrystallization from dimethyl sulfoxide and drying under high vacuum and refluxing xylenes for four days yielded 4.6 g of pale yellow microcrystals, m.p. >250° C.

Analysis: Calculated for C$_{30}$H$_{16}$N$_4$: 76.90%C, 5.16%H, 17.94%N, Found: 76.54%C, 5.21%H, 17.88%N.

EXAMPLE 14

2,11-Diamino-4,5-dihydro-2H-pyrazolo[3,4-a]acridine

To a suspension of 11-amino-4,5-dihydro-1H-pyrazolo[3,4-a]acridine (40.0 g) in an aqueous sodium hydroxide solution (37.1 g in 561 ml of water) at 50° C.

was added ethanol (1550 ml). The resulting solution was heated to 55° C. and solid hydroxylamine-o-sulfonic acid (51.6 g) was added in portions over 15 minutes. The reaction was stirred for a half hour without heat, the resulting solid was filtered, washed with water, boiled in methanol (1500 ml), filtered hot to remove inorganics, concentrated, and triturated with diethyl ether to yield 5.79 g of a product containing approximately 20% of the starting material which was inseparable by chromatography.

A 5.0 g portion of the mixture was stirred in benzaldehyde (168 ml) at room temperature for three hours, diluted with pentane (700 ml), stirred mechanically for three hours, filtered, and triturated with pentane to yield 9.93 g of the crude benzylidene derivative, namely, 11-amino-2-benzylideneamino-4,5-dihydro-2H-pyrazolo[3,4-a]acridine. The solid was adhered to silica and flash chromatographed twice (EtOAc; 5% Et$_3$N/toluene) to yield 3.7 g of pure benzylidene derivative. A 3.2 g portion of the benzylidene derivative was refluxed in hydrazine monohydrate (12.8 ml) and n-butanol (96 ml) overnight. The reaction was cooled to room temperature, diluted with diethyl ether (100 ml), filtered, and washed with diethyl ether to yield 2.33 g of the title compound in a wet condition. Drying under high vacuum and refluxing xylenes overnight yielded 2.0 g of 2,11-diamino-4,5-dihydro-2H-pyrazolo[3,4-a]acridine as a crystalline solid, mp>250° C.

Analysis: Calculated for C$_{14}$H$_{13}$N$_5$: 66.92%C, 5.21%H, 27.87%N, Found: 66.70%C, 5.18%H, 27.79%N.

EXAMPLE 15

11-Amino-2-benzylideneamino-4,5-dihydro-α-phenyl-2-H pyrazolo[3,4-a]acridine-5-methanol To a warm suspension (50° C.) of 11-amino-4,5-dihydro-1H-pyrazolo[3,4-a]acridine (26.77 g) and solid sodium hydroxide (24.9 g) in water (377 ml) was added ethanol (1133 ml). Hydroxylamine-o-sulfonic acid (34.27 g) was added in portions over 15 minutes and the reaction was cooled to room temperature. The resulting solid was filtered, washed with water, air dried, heated with excess benzaldehyde, filtered to remove insolubles, concentrated, and triturated (diethyl ether) to yield 10.32 g of a mixture of the target product and 11-amino-2-benzylideneamino-4,5-dihydro-2H-pyrazolo[3,4-a]acridine.

A 5.0 g portion of the mixture was stirred in benzaldehyde (100 ml) at 50° C. for four hours, filtered hot, and washed with benzaldehyde and diethyl ether to yield 5.15 g of the target product. Recrystallization from methanol/methylene chloride gave 2.67 g of clean product. However, upon drying sight decomposition occurred. Flash chromatography (10–50% EtOAc/CH$_2$/Cl$_2$) and trituration (pentane) yielded 1.42 g (5.6%) of a pale yellow fluffy solid, m.p. 154°156° C.

Analysis: Calculated for C$_{28}$H$_{23}$H$_5$O: 75.49%C, 5.20%H, 15.72%N, Found: 75.20%C, 5.23%H, 15.61%N.

EXAMPLE 16

4,5-Dihydro-2H-pyrazolo[3,4-a]acridine 3,4-Dihydroacridin-1(2H)-one (19.43 g) was refluxed in N,N-dimethylformamide dimethyl acetal (48.57 ml) and triethylamine (13.76 ml) for 10 hours. The reaction was concentrated and thereafter, triturated first with diethyl ether/pentane and then with diethyl ether, to yield 22.43 g of 2-(dimethylaminomethylene)-3,4-dihydroacridin-1(2H)-one. This was combined with an additional 1.07 g of compound and refluxed in hydrazine (12.68 ml) and ethanol (372 ml) for 2.5 hours. The reaction was cooled, concentrated, and triturated with diethyl ether to yield 20.67 g of a pale orange crystalline solid. A 3.5 g portion was recrystallized from methanol and dried under high vacuum and refluxing xylenes for 30 hours to yield 1.60 g of an off-white crystalline solid, mp 248°–248.5° C.

Analysis: Calculated for C$_{14}$H$_{11}$N$_3$: 76.00%C, 5.01%H, 18.99%N, Found: 76.12%C, 4.99%H, 19.02%N.

EXAMPLE 17

2-Amino-4,5-dihydro-2H-pyrazolo[3,4-a]acridine

To a suspension of 4,5-dihydro-2H-pyrazolo[3,4-a]acridine (12.60 g) in an aqueous sodium hydroxide solution (12.52 g in 189 mL of water) at 50° C. was added ethanol (200 mL). The resulting solution was heated to 60° C. and solid hydroxylamine-o-sulfonic acid (17.72 g) was added in portions over 15 minutes. The reaction was stirred for 45 minutes without heat, diluted with water (500 mL), stirred for a half hour, filtered, washed with water, and air dried to yield 12.28 g of an inseparable mixture of target product, starting material, and the minor 1-amino isomer.

A 11.2 g portion of this mixture was stirred in benzaldehyde (168 mL) and triethylamine (13.44 mL) at room temperature overnight and flash chromatographed (0–30% EtOAc/Hexane) to yield 7.92 g of the benzylidene derivative. A 6.0 g portion was refluxed in hydrazine (24 ml) and n-butanol (120 mL) for 6.5 hours, concentrated, adhered to silica (methanol), and flash chromatographed (0–60% EtOAc/hexane; 60% EtOAc/hexane-0.6% Et$_3$N) to yield 1.8 g of clean target product. This was combined with an additional 336 mg of product, recrystallized from ethanol and dried under high vacuum and refluxing toluene overnight to yield 1.6 g of a peach colored solid, mp 184°–185° C.

Analysis: Calculated for C$_{14}$H$_{12}$N$_4$: 71.17%C, 5.12%H, 23.71%N, Found: 71.07%C, 5.12%H, 23.61%N.

EXAMPLE 18

1-Amino-4,5-dihydro-1H-pyrazolo[3,4-a]acridine

To a suspension of 4,5-dihydro-2H-pyrazolo[3,4-a]acridine (12.60 g) in an aqueous sodium hydroxide solution (12.52 g in 189 mL of water) at 50° C. was added ethanol (200 mL). The resulting solution was heated to 60° C. and solid hydroxylamine-o-sulfonic acid (17.72 g) was added in portions over 15 minutes. The reaction was stirred for 45 minutes without heat, diluted with water (500 mL), stirred for a half hour, filtered, washed with water, and air dried to yield 12.28 g of an inseparable mixture of the starting material, the major 2-amino and the minor 1-amino isomers.

A 11.2 g portion of this mixture was stirred in benzaldehyde (168 mL) and triethylamine (13.44 mL) at room temperature overnight and flash chromatographed (0–30% EtOAc/hexane; 5% Et$_3$N/EtOAc) to yield 7.92 g of the 2-benzylideneamino compound and 200 mg of clean product. The mixed fractions were concentrated and flash chromatographed (20–60% EtOAc/hexane; 60% EtOAc/hexane-0.6% Et$_3$N) to yield an additional 387 mg of product. The combined product was treated with "darco" in boiling ethanol, filtered through celite, concentrated and recrystallized from ethanol to yield 330 mg of off-white crystals, mp. 235° C.

Analysis: Calculated for $C_{14}H_{12}N_4$: 71.17%C, 5.12%H, 23.71%N, Found: 70.89%C, 4.96%H, 23.57%N.

We claim:

1. A compound having the formula,

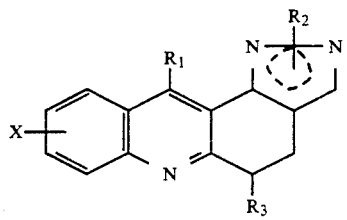

where,

X is hydrogen, loweralkyl, loweralkoxy, halogen or trifluoromethyl;

$R_1$ is hydrogen or $-NR_4R_5$, each of $R_4$ and $R_5$ being independently hydrogen, loweralkyl or aryllower-alkyl;

$R_2$ which is a substituent on one of the two nitrogen atoms of the pyrazole ring, is hydrogen, loweralkyl, loweralkenyl, aryl, arylloweralkyl, cyanoloweralkyl, $-C_mH_{2m}COOR_6$, $-NR_7R_8$, $-C_nH_{2n}NR_7R_8$ or $-N=CH$-aryl, $R_6$ being hydrogen or loweralkyl, m being an integer of 1 to 3, each of $R_7$ and $R_8$ being independently hydrogen or loweralkyl, and n being an integer of 2 and 4; and $R_3$ is hydrogen or $-CHOH$-aryl; the term "aryl" in each occurrence signifying a phenyl group optionally mono-substituted with loweralkyl, loweralkoxy, halogen or trifluoromethyl;

or a pharmaceutically acceptable acid addition salt thereof.

2. The compound as defined in claim 1, which is 11-amino-4,5-dihydro-1H-pyrazolo[3,4-a]acridine.

3. The compound as defined in claim 1, which is 11-amino-4,5-dihydro-2H-pyrazolo[3,4-a]acridine.

4. The compound as defined in claim 1, which is 11-amino-4,5-dihydro-2-propyl-2H-pyrazolo[3,4-a[acridine.

5. The compound as defined in claim 1, which is 11-amino-4,5-dihydro-2-(2-phenylethyl)-2H-pyrazolo[3,4-a]acridine.

6. The compound as defined in claim 1, which is 11-amino-4,5-dihydro-2H-pyrazolo[3,4-a]acridine-2-acetic acid ethyl ester.

7. The compound as defined in claim 1, which is 11-amino-4,5-dihydro-2H-pyrazolo[3,4-a]acridine-2-acetic acid.

8. The compound as defined in claim 1, which is 11-amino-4,5-dihydro-2-(2-dimethylaminoethyl)-2H-pyrazolo[3,4-a]acridine.

9. The compound as defined in claim 1, which is 11-amino-2-benzyl-4,5-dihydro-2H-pyrazolo[3,4-a]acridine.

10. The compound as defined in claim 1, which is 11-amino-4,5-dihydro-2H-pyrazolo[3,4-a]acridine-2-acetonitrile.

11. The compound as defined in claim 1, which is 11-amino-4,5-dihydro-2-(2-propenyl)-2H-pyrazolo[3,4-a]acridine.

12. The compound as defined in claim 1, which is 11-amino-4,5-dihydro-1-methyl-1H-pyrazolo[3,4-a]acridine.

13. The compound as defined in claim 1, which is 11-amino-4,5-dihydro-2-methyl-2H-pyrazolo[3,4-a]acridine.

14. The compound as defined in claim 1, which is 11-amino-4,5-dihydro-1-phenyl-1H-pyrazolo[3,4-a]acridine.

15. The compound as defined in claim 1, which is 2,11-diamino-4,5-dihydro-2H-pyrazolo[3,4-a]acridine.

16. The compound as defined in claim 1, which is 11-amino-2-benzylideneamino-4,5-dihydro-α-phenyl-2H-pyrazolo[3,4-a[acridine-5-methanol.

17. The compound as defined in claim 1, which is 4,5-Dihydro-2H-pyrazolo[3,4-a]acridine.

18. The compound as defined in claim 1, which is 2-amino-4,5-dihydro-2H-pyrazolo[3,4-a]acridine.

19. The compound as defined in claim 1, which is 1-amino-4,5-dihydro-1H-pyrazolo[3,4-a]acridine.

20. An analgesic composition comprising an effective pain-alleviating amount of a compound as defined in claim 1 and a suitable carrier therefor.

21. A method of treating a patient in need of relief from pain which comprises administering to the patient an effective pain-alleviating amount of a compound as defined in claim 1.

* * * * *